United States Patent [19]

DiCosimo et al.

[11] Patent Number: 5,728,556
[45] Date of Patent: Mar. 17, 1998

[54] PRODUCTION OF ω-CYANOCARBOXAMIDES FROM ALIPHATIC α,ω-DINITRILES USING PSEUDOMONAS PUTIDA-DERIVED BIOCATALYSTS

[75] Inventors: Robert DiCosimo, Wilmington, Del.; Barry Stieglitz, Wynnewood, Pa.; Robert D. Fallon, Elkton, Md.

[73] Assignee: E. I. du Pont de Nemours and Company, Wilmington, Del.

[21] Appl. No.: 615,365

[22] Filed: Mar. 14, 1996

[51] Int. Cl.$^6$ .................................................. C12P 13/02
[52] U.S. Cl. ...................... 435/129; 435/227; 435/253.3; 435/877
[58] Field of Search .................................. 435/129, 877, 435/253.3, 227, 232

[56] References Cited

U.S. PATENT DOCUMENTS

| | | | |
|---|---|---|---|
| 4,366,250 | 12/1982 | Jallageas et al. | 435/280 |
| 4,390,631 | 6/1983 | Watanabe et al. | 435/244 |
| 4,629,700 | 12/1986 | Prevatt et al. | 435/128 |
| 4,637,982 | 1/1987 | Yamada et al. | 435/129 |
| 4,908,313 | 3/1990 | Satoh et al. | 435/129 |
| 4,931,391 | 6/1990 | Enomoto et al. | 435/188 |
| 5,179,014 | 1/1993 | Watanabe et al. | 435/129 |
| 5,200,331 | 4/1993 | Kawakami et al. | 435/129 |
| 5,334,519 | 8/1994 | Yamada et al. | 435/129 |

FOREIGN PATENT DOCUMENTS

| | | | |
|---|---|---|---|
| 0 178 106 B1 | 4/1986 | European Pat. Off. | C12P 13/00 |
| 0 502 476 A2 | 9/1992 | European Pat. Off. | C12N 15/74 |
| 6-81597 | 6/1990 | Japan | C12P 13/02 |
| WO 92/05275 | 4/1992 | WIPO | C12P 41/00 |
| WO 95/04828 | 2/1995 | WIPO | C12N 15/60 |

OTHER PUBLICATIONS

Yamada, et al, *J. Ferment. Technol.*, 58(6), 495–500 (1980).
Derwent Abstract Biotech 96–11928, JP08154691 (Jun. 18, 1996) Sumitomo Chem.
Derwent Abstract Biotech 82–00324, Asano et al, "Agricult. Biot. Chem" 1982 No. 5, pp. 1183–1189.

*Primary Examiner*—Herbert J. Lilling

[57] ABSTRACT

Applicants have provided methods for obtaining aliphatic omega-cyanocaboximides of Formula I $$NC\text{—}CH(R_1)(CH)_n CH(R_2)C(O)NH_2$$

wherein n=1–8 and $R_1$ or $R_2$ are either H or $CH_3$.
from dinitriles of Formula II $$NC\text{—}CH(R_1)(CH)_n CH(R_2)CN$$

wherein n=1–8 and $R_1$ or $R_2$ are either H or $CH_3$,
using biocatalysts which have regioselective nitrile hydratase activity and which are derived from members of the bacterial species *Pseudomonas putida*.

9 Claims, No Drawings

PRODUCTION OF ω-CYANOCARBOXAMIDES FROM ALIPHATIC α,ω-DINITRILES USING PSEUDOMONAS PUTIDA-DERIVED BIOCATALYSTS

FIELD OF THE INVENTION

The invention relates to production of aliphatic ω-cyanocarboxamides from α,ω-dinitriles using a *Pseudomonas putida*-derived biocatalyst.

DESCRIPTION OF RELATED ART

The hydrolysis of nitriles has long been useful for the production of various amide intermediates in processes for making polymers such as nylon and polyacrylamide. Processes involving enzymatic conversion of nitrile substrates are sometimes favored over chemical synthesis for their production of fewer harmful reaction by-products and for greater reaction specificity.

The occurrence of nitrile hydrolyzing enzymes has been widely described. Within this family of enzymes, two broad classes are generally recognized. The first includes the nitrile hydratases which catalyze the addition of one molecule of water to the nitrile, resulting in the formation of the corresponding amide:

Reaction 1

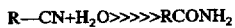
R—CN+H$_2$O>>>>>RCONH$_2$

The second group includes the nitrilases which catalyze the addition of two molecules of water to the nitrile resulting in the direct formation of the corresponding carboxylic acid plus ammonia, without the intermediate formation of the corresponding amide:

Reaction 2

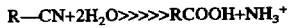
R—CN+2H$_2$O>>>>>RCOOH+NH$_3^+$

In addition, all known organisms containing nitrile hydratases (Reaction 1) also contain an amidase enzyme, capable of catalyzing the addition of one molecule of water to the amide resulting in the formation of the corresponding carboxylic acid plus ammonia:

Reaction 3

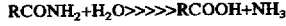
RCONH$_2$+H$_2$O>>>>>RCOOH+NH$_3$

For the purposes of industrial processes, the presence of this amidase activity in biocatalysts capable of carrying out Reaction 1, may or may not be desirable.

A wide variety of bacterial genera are known to possess nitrile hydratase and amidase activities including Rhodococcus, Pseudomonas, Alcaligenes, Arthrobacter, Bacillus, Bacteridium, Brevibacterium, Corynebacterium, and Micrococcus. Wild type microorganisms known to possess nitrile hydratase activity have been used to convert nitriles to amides and carboxylic acids. The enzymatic hydrolysis of aliphatic nitriles by methods employing bacterial strains of the above mentioned genera is well known. For example, U.S. Pat. Nos. 5,179,014, 5,200,331, and 5,334,519 teach processes for enzymatic hydration of aliphatic or aromatic nitriles having 2 to 8 carbon atoms to the corresponding amide using strains of Rhodococcus. Similarly, U.S. Pat. No. 4,637,982 of Yamada et al. which issued Jan. 20, 1987, teaches a process for enzymatic hydration of aliphatic nitriles having 2 to 4 carbons using a strain of Pseudomonas. U.S. Pat. No. 4,366,250 teaches the use of Bacillus, Bacteridium, Micrococcus and Brevibacterium in a method for the preparation of L-amino acids from the corresponding racemic amino nitriles. Finally, in WO 92/05275 the Applicants teach a biologically-catalyzed method for converting a racemic alkyl nitrile to the corresponding R- or S-alkanoic acid through an intermediate amide using members of the bacterial genera Pseudomonas spp. (e.g., *putida, aureofaciens*, Moraxella spp.) and Serratia (e.g., *Serratia liquefaciens*).

In addition to the use of wild type organisms, recombinant organisms containing heterologous genes for the expression of nitrile hydratase are also known for the conversion of nitriles. For example, Cerebelaud et al. (WO 95/04828) teach the expression in *E. coli* of nitrile hydratase genes isolated from *C. testosteroni*. The transformed hosts effectively convert nitriles to amides where the nitrile substrate contains one nitrile and one carboxylate group. Similarly, Beppu et al. (EP 5024576) disclose plasmids carrying both nitrile hydratase and amidase genes from Rhodococcus capable of transforming *E. coli* where the transformed host is then able to use isobutyronitrile and isobutyramide as enzymatic substrates.

Heterobifuntional compounds are useful as polymer intermediates as well as intermediates in high value agricultural or pharmaceutical products. From aliphatic, α,ω-dinitriles, it is sometimes desirable to produce such heterobifunctional compounds by hydrolyzing a single functional group without further modification, for example, Reaction 4

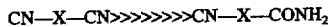
CN—X—CN>>>>>>>>CN—X—CONH$_2$ where X is a $C_1$–$C_8$ or an allicyclic or aromatic six carbon ring. Such "regioselectivity" is often beyond the capability of chemical catalysts. However, biocatalysts are often capable of recognizing subtle structural differences which may allow useful regioselective biocatalysts to be developed. In the case described, such a process requires a biocatalyst with both a nitrile hydratase of proper selectivity and the absence of amidase activity that could result in further hydrolysis of the amide. In the field of nitrile biocatalysts, few such regioselective biocatalysts resulting in ω-cyanocarboxamide compounds have been described. For example, European Patent Application 178 106, published Apr. 16, 1986, discloses selective transformation of one of the cyano groups of a dinitrile to the corresponding carboxylic acid, amide, ester or thioester using a mononitrilase derived from Bacillus, Bacteridium, Micrococcus or Brevibacterium. JP 02154692 describes the conversion of some aliphatic dinitriles (<$C_8$) to the corresponding ω-cyanocarboxamide derivatives using Acinetobacter strain (FERM P-10432). U.S. Pat. No. 4,629,700 describes conversion of aromatic dinitriles to the corresponding mono or diamides using Rhodococcus strains. The use of biocatalysts from the Pseudomonas genus for the regioselective conversions of dinitriles to aliphatic omega-cyanocarboxamides has not been anticipated in the art. The only previous report of dinitrile conversion by a Pseudomonas strain comments that only minor amounts of the heterobifunctional compounds cyanobutyric acid and cyanobutyramide were detected, while glutaric acid was the major product detected following glutaronitrile (a $C_4$ dinitrile) hydrolysis by Pseudomonas sp. K9 (Yamada et al., *J. Ferment. Technol.* 58(6):495–500, 1980). High levels of amidase activity caused rapid diacid formation, making the strain useless as a biocatalyst for ω-cyanocarboxamide production.

Pseudomonas strains often show growth rates faster than other microbes known in the art as biocatalysts useful in producing ω-cyanocarboxamides. Rapid growth makes biocatalyst production more efficient. Therefore, the ability to produce Pseudomonas-derived biocatalysts leads to a more efficient overall process for ω-cyanocarboxamide production.

SUMMARY OF THE INVENTION

The invention relates to a method to produce aliphatic ω-cyanocarboxamides of Formula I $$NC-CH(R_1)(CH)_nCH(R_2)C(O)NH_2$$

where n=1–8 and $R_1$ or $R_2$ are either H or $CH_3$, from aliphatic α,ω-dinitriles of Formula II $$NC-CH(R_1)(CH)_nCH(R_2)CN$$

where n=1–8 and $R_1$ or $R_2$ are either H or $CH_3$, using biocatalysts having regioselective nitrile hydratase activity derived from *Pseudomonas putida* and recovering the aliphatic ω-cyanocarboxamides from the medium.

In one embodiment, biocatalysts derived from *Pseudomonas putida* are capable of producing ω-cyanocarboxamide products from dinitriles without significant by-product production, increasing the yield of ω-cyanocarboxamides relative to that obtained when using non-regioselective biocatalysts.

In a specific embodiment, 5-cyanopentanamide is produced from adiponitrile with a product:byproduct ratio (5-cyanovaleramide:adipamide) of ≥30:1 at various temperatures and starting concentrations of adiponitile, using regioselective biocatalysts derived from *P. putida* 3L-G-1-5-1a-1 (ATCC 55736).

In another specific embodiment, 4-cyannopentanamide and 4-cyano-2-methylbutyramide are produced from 2-methylglutaronitrile with a product:byproduct ratio (4-methyl-4-cyanobutyramide and 2-methyl-4-cyanobutyramide:2-methylglutaramide) of ≥15:1 at various temperatures and starting concentrations using biocatalysts derived from *P. putida* 3L-G-1-5-1a-1 (ATCC 55736).

In a third specific embodiment, 5-cyanopentanamide is produced from adiponitrile with a product:byproduct ratio of ≥100:1 at 30° C. and various starting concentrations of adiponitile using biocatalysts derived from *P. putida* 20-5-SBN-1b (ATCC 55735).

BRIEF DESCRIPTION OF THE BIOLOGICAL DEPOSITS

Applicants have made the following biological deposits under the terms of the Budapest Treaty:

| Depositor Strain Designation | International Depository Accession No. | Date of Deposit |
|---|---|---|
| *Pseudomonas putida* 3L-G-1-5-1a-1 | ATCC 55736 | 26 January 1996 |
| *Pseudomonas putida* 20-5-SBN-1b | ATCC 55735 | 26 January 1996 |

As used herein, "ATCC" refers to the American Type Culture Collection international depository located at 12301 Parklawn Drive, Rockville, Md. 20852, U.S.A. The "ATCC No." is the accession number to cultures on deposit with the ATCC.

DETAILED DESCRIPTION OF THE INVENTION

The present invention recites a process for the production of aliphatic ω-cyanocarboxamides from α,ω-dinitriles utilizing biocatalysts derived from *Pseduomonas putida* having regioselective nitrile hydratase activity. The products of the present invention are useful primarily as precursors for polymers, solvents, and chemicals of high value in the agricultural and pharmaceutical industries.

The following definitions will be used for interpretation of the claims and specification.

The term "product:byproduct ratio" refers to the weight or molar ratio of desirable reaction product(s) to undesirable reaction product(s).

The term "nitrile hydratase", abbreviated "NHase", will refer to an enzyme capable of catalyzing the following reaction: $R-CN+H_2O>>>>>RCONH_2$.

The terms "omega-cyanocarboxamide" or "ω-cyanocarboxamide" will refer to a chemical compound of the formula $NC-R-C(O)NH_2$.

Abbreviations of substrate or product names are as follows:

4-CMBAM 4-cyano-2-methylbutyramide
4-CPAM 4-cyanopentanamide
2-MGN 2-methylglutaronile
2-MGAM 2-methylglutaramide
ADN adiponitrile The term "biocatalyst" refers to any substance, organic matter, compound or mixtures of compounds, derived from a biological source, which is capable of catalyzing a specific desired chemical reaction. Biocatalysts may be purified enzymes, partially purified enzymes, crude cell lysates or whole cells. Biocatalysts that include whole cells will be referred to as: "whole cell biocatalysts" or "whole cell catalysts". Whole cell catalysts may be either living or dead cells and may be utilized either in free suspension or immobilized on a suitable support. Immobilized catalysts of this sort will be referred to as "immobilized whole cell catalysts". Biocatalysts of particular significance within the context of the present invention are derived from *Pseudomonas putida* and will be referred to as "*Pseudomonas putida*-derived biocatalysts". The term "derived" is used to indicate the source of the biocatalyst regardless of the particular form used (i.e., whole cells, organic material, crude cell lysates, or purified or partially purified enzymes, either in free suspension or immobilized).

As used herein, "NRRL" refers to the Northern Regional Research Laboratory, Agricultural Research Service Culture Collection international depository located at 11815 N. University Street, Peoria, Ill. 61604, U.S.A. The "NRRL No." is the accession number to cultures on deposit at the NRRL.

As used herein, "FERM" refers to The Fermentation Research Institute, now known as The National Institute of Bioscience and Human Technology (NIBHT), Agency of Industrial Science and Technology, Ministry of International Trade and Industry, 1-3, higashi 1-chome, Tsukuka-shi, Ibaraki-ken 305, Japan. The "FERM No." is the accession number to cultures on deposit with the FERM.

Biocatalysts useful in the described process are very selective for the hydrolysis of α,ω-dinitriles to the corresponding ω-cyanocarboxamides. Biocatalysts yielding a ω-cyanocarboxamides:by-product ratio of >5:1 may be useful in such a process with preferred biocatalysts showing a ratio of >20: 1. The nitrile hydratase activity of *P. putida*

3L-G-1-5-1a-1 (ATCC 55736) cells is very selective for the hydrolysis of α,ω-dinitriles to the corresponding ω-cyanocarboxamides. This catalyst hydrolyzes adiponitrile to 5-cyanopentanamide in high yield, with adipamide being the only by-product produced in the reaction. The ratio of 5-cyanopentanamide to adipamide observed over the course of the adiponitrile hydrolysis reaction is typically 50:1 (molar ratio), with a selectivity to 5-cyanopentanamide of ca. 98% at 100% conversion of adiponitrile. The whole cells can be used as catalyst in a reaction mixture without any pretreatment or they can be immobilized in a polymer matrix (e.g., alginate beads or polyacrylamide gel (PAG) particles) or on an insoluble solid support (e.g., controlled-pore glass) to facilitate recovery and reuse of the catalyst. Methods for the immobilization of cells in a polymer matrix or on an insoluble solid support have been widely reported and are well-known to those skilled in the art (Chibata et al., (1986), Methods of Cell Immobilization, Ch. 18 in Manual of Industrial Microbiology, A. L. Demain & N. A. Solomon (ed.), ASM, Washington, DC). The nitrile hydratase enzyme separated from the whole cells can also be used directly as catalyst, or the enzyme can be immobilized in a polymer matrix or on an insoluble support. These methods have also been widely reported and are well-known to those skilled in the art (Bernath et al., (1986), Methods of Enzyme Immobilization, Ch. 19 in Manual of Industrial Microbiology, A. L. Demain & N. A. Solomon(ed.), ASM, Washington, DC).

When the nitrile hydratase activity of *P. putida* 3L-G-1-5-1a-1 (ATCC 55736) cells is used to hydrolyze the unsymmetrically-substituted 2-methylglutaronitrile (2-MGN), the corresponding ω-cyanocarboxamides 4-cyano-2-methylbutyramide (4-CMBAM) and 4-cyanopentanamide (4-CPAM) are produced with high selectivity, with 2-methylglutaramide (2-MGAM) being the only by-product produced in the reaction:

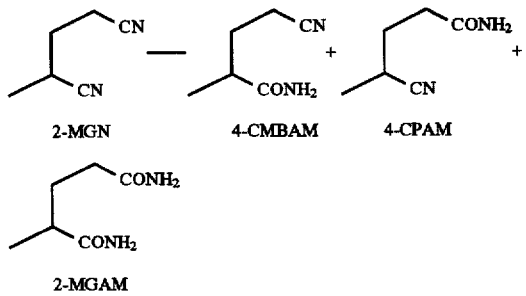

The ratio of 4-CMBAM to 4-CPAM produced over the course of the hydrolysis reaction is ca. 2.4:1, and the selectivity to the ω-cyanocarboxamides is typically 95% at 100% conversion of 2-methylglutaronitrile, with an additional 5% selectivity to 2-methylglutaramide.

In the accompanying Examples, any reaction mixture containing amounts of dinitrile which exceed the solubility of the dinitrile under the described reaction conditions will be a two-phase reaction (aqueous phase and non-aqueous phase). Many dinitriles are only moderately water-soluble and solubility is affected by temperature and salt concentration of the aqueous phase. For example, adiponitrile has a solubility limit (25° C., 20 mM phosphate buffer, pH 7) of 0.597M and under the same conditions 2-methylglutaronitrile has a solubility limit of 0.52M. As a result, reaction mixtures may contain an aqueous and non-aqueous phase. Although the appearance of reaction mixture is altered, there is no affect on the selectivity of the α,ω-dinitrile conversion to ω-cyanocarboxamides. The nitrile dissolves into the aqueous phase as the reaction progresses and a single phase reaction is eventually obtained.

The desired aliphatic omega-cyanocarboxamide product is recovered using techniques common to the art. At the conclusion of the reaction, where the conversion of the dinitrile is typically >95%, the resulting aqueous mixture is centrifuged and the biocatalyst is recovered for reuse in a subsequent reaction. The resulting supernatant is filtered, and the volume of the supernatant may be concentrated by removal of water (for example, by rotary evaporation under reduced pressure). The ω-cyanocarboxamide product(s) is isolated from the supernatant (or concentrated supernatant) by extraction with a suitable organic solvent in which the product nitrile amide is preferentially soluble (e.g., ethyl acetate). The combined organic extracts are then combined, stirred with a suitable drying agent (e.g., magnesium sulfate), filtered, and the solvent removed (e.g., by rotary evaporation) to produce the desired product in high yield and in high purity (typically 98–99% pure). If desired, the product nitrile amide can be further purified by recrystallization or distillation. In the case of 5-cyanopentanamide, or the mixture of ω-cyanocarboxamides produced from the hydrolysis of 2-methylglutaronitrile, recrystallization from ethyl acetate or toluene results in ω-cyanocarboxamide purities in excess of 99.5%.

EXAMPLES

Materials and Methods

Identification and Isolation of Biocatalysts

The microorganisms used in the present invention belong to the genus Pseudomonas. Representative *Pseudomonas putida* strains are listed above in the Brief Description of the Biological Deposits. In addition, the following Pseudomonas strains were found to produce the desired product: *P. putida* 5B-MGN-2p (NRRL-18668), *P. putida* 3L-H-2-6-1p, *P. chlororaphis* B23 (FERM-B 187), Pseudomonas sp. 3L-H-9-6-2p, and *P. putida* 2-H-9-5-1a.

With the exception of *P. chlororaphis* B23, all of the strains used by the Applicants were isolated from soil collected in Orange, Tex. Standard enrichment procedures were used with the following medium (PR Basal Medium, pH 7.2).

| PR Basal Medium | g/L |
| --- | --- |
| $KH_2PO_4$ | 8.85 |
| Sodium citrate | 0.225 |
| $MgSO_4 7H_2O$ | 0.5 |
| $FeSO_4 7H_2O$ | 0.05 |
| $FeCl_2 4H_2O$ | 0.0015 |
| $CoCl_2 6H_2O$ | 0.0002 |
| $MnCl_2 4H_2O$ | 0.0001 |
| $ZnCl_2$ | 0.00007 |
| $H_3BO_3$ | 0.000062 |
| $NaMoO_4 2H_2O$ | 0.000036 |
| $NiCl_2 6H_2O$ | 0.000024 |
| $CuCl_2 2H_2O$ | 0.000017 |
| Biotin | 0.00001 |
| Folic Acid | 0.00005 |
| Pyridoxine.HCl | 0.000025 |
| Riboflavine | 0.000025 |
| Nicotinic Acid | 0.000025 |
| Pantothenic Acid | 0.00025 |
| Vitamin B12 | 0.000007 |
| p-Aminobenzoic Acid | 0.00025 |

The following modifications were made to the PR basal medium for the enrichments described above:

| Strain | Enrichment Nitrile (25 mM) | Other |
| --- | --- | --- |
| 3L-G-1-5-1a-1 (ATCC 55736) | 2-methylglutaronitrile (2-MGN) (Aldrich Chemical Co., Milwaukee, WI) | pH 5.6 |
| 5B-MGN-2p (NRRL-18668) | 2-methylglutaronitrile (2-MGN) | pH 5.6 |
| 3L-H-2-6-1p | acetonitrile (Aldrich Chemical Co., Milwaukee, WI) | |
| 20-5-SBN-1b (ATCC 55735) | S-methylbutyronitrile (Aldrich Chemical Co., Milwaukee, WI) | |
| 3L-H-9-6-2p | undecylcyanide (Aldrich Chemical Co., Milwaukee, WI) | pH 5.6 |
| 2-H-9-5-1a | undecylcyanide | |

Strains were originally selected based on growth and ammonia production on the enrichment nitrile. Isolates were purified by repeated passing on Bacto Brain Heart Infusion Agar (Difco, Detroit, Mich.) followed by screening for ammonia production from the enrichment nitrile. Purified strains were identified by Acculab (Newark, Del., USA) based on their membrane fatty acid profiles by gas chromatography using Sherlock, v. 1.06, software and databases.

Microorganism Screening for Nitrile Hydrolysis Activity

For testing nitrile hydrolysis activity, PR basal medium with 10 g/L glucose was used to grow cell material. The medium was supplemented with 25 mM 2-methylglutaronitrile. A 10 mL inoculum of supplemented PR medium was inoculated with 0.1 mL of frozen stock culture. Following overnight growth at room temperature (22°–25° C.) on a shaker at 250 rpm, the 10 mL inoculum was added to 990 mL of fresh medium in a 2 L flask. The cells were grown overnight at room temperature with stirring at a rate high enough to cause bubble formation in the medium. Cells were harvested by centrifugation, washed once with 50 mM phosphate buffer (pH 7.2)/15% glycerol and the concentrated cell paste was immediately frozen on dry ice and stored at –65° C. Thawed cell pastes were used for testing nitrile hydrolysis activity. The microorganism should contain the desired regioselective nitrile hydrolyzing in the absence of significant interfering amidase activity. Mutation is a natural pheneomenon in microorganisms. Mutations favoring this desirable property might be found in the native strain, leading to enhanced regioselective NHase activity or to decreased non-regioselective Nhase activity or decreased amidase activity. Thus, even mutants of the native strain may be used to carry out the process of the instant invention. Finally, the regioselective NHase enzymes may also be produced in non-native microbial strains through techniques common to the art of genetic engineering (Sambrook et al. (1989), Molecular Cloning, 2rid Ed., V. 1, 2, & 3; Cold Spring Harbor Laboratory Press, USA) leading to the production of desirable biocatalysts.

Selection of Microbial Biocatalysts

To produce biocatalyst for process demonstration (as for Examples 2, 3, 4, 5, 6, 7 and 8), a vial containing 10 mL of PR medium with 1% glucose, 0.001% yeast extract and 10 mM butyronitrile was inoculated with 0.1 mL of frozen stock culture. Following overnight growth at 30° C. with shaking at 250 rpm, the growing cell suspension was transferred to 1 L of the same medium in a 2 L flask and growth continued at 30° C. with shaking. The 1 L growing cell suspension was then added to 9 L of the same medium in a 10 L fermentation vessel where growth continued overnight. Nominal conditions in the fermenter were: ≧80% oxygen saturation, 25° C., pH 7.2, 300–1000 rpm. After 14–23 hours, the vessel was chilled to 8°–12° C. and glycerol added to 10% final concentration. Cells were harvested by centrifugation. The concentrated cell paste was immediately frozen on dry ice and stored at –70° C. until use.

In addition, 1 L fermentations were carried out for biocatalyst production (as for Examples 1, 9 and 10). The process described above was followed with the following modifications. Adiponitrile, 10 mM, was used in the fermentations. Fermentations were stopped after 16–20 hours of growth at the 1 L stage. The cell suspension was chilled to 4° C., harvested by centrifugation and frozen at –60° C. following one wash with 15% glycerol in 0.05M phosphate buffer, pH 7.2.

Assay for Nitrile Hydratase Activity

The specific nitrile hydratase (NHase) activity (catalyst activity/gram cells) of 3L-G-1-5-1a-1 (ATCC 55736) whole cells was determined using a spectrophotometric assay. The assay protocol was to add 0.020 mL of a 10 mg/mL suspension of cells in 100 mM $KH_2PO_4$ buffer (pH 7.0) to a 3 mL quartz cuvette containing 2.0 mL of 10 mM methacrylonitrile/100 mM $KH_2PO_4$ buffer (pH 7.0) and a magnetic stir bar, followed by stirring the resulting suspension at 27° C. while recording the change in absorbance at 224 nm ($\epsilon$=3400 L $mol^{-1}$ $cm^{-1}$). Nitrile hydratase activities are reported in IU/gram wet cell weight, where one IU (International Unit) of enzyme activity is equivalent to the amount of enzyme which will hydrolyze 1 micromole/minute of methacrylonitrile.

For Examples 2–8, the hydrolysis products of adiponitrile or 2-methylglutaronitrile were analyzed by high pressure liquid chromatography (HPLC) using techniques common to the art (Snyder et al., (1979), Introduction to Liquid Chromatography. John Wiley & Sons, NY). Specifically, Applicants used a refractive index detector and a Supelcosil LC-18-DB column (25 cm×4.6 mm dia.) (Supelco, Inc., Bellefonte, Pa., USA) with a mobile phase of 10 mM acetic acid/10 mM sodium acetate/2.5% methanol in water at a flow rate of 1.0 mL/min. In addition, for some examples, the hydrolysis products of adiponitrile were analyzed by gas chromatography (GC) using techniques common to the art (MeNair et al., (1965), Basic Gas Chromatography). Specifically, Applicants used an HP-17 crosslinked 50% PH ME silicone chromatography column in an HP 5890 gas chromatograph with FID detector. A temperature program of 180° C. for 1 min followed by a temperature increase of 10° C./min to a final temperature of 240° C. with 1 min hold was used to aid in peak resolution. Gas chromatography data are an average of duplicate determinations. Retention times were determined from authentic standards. N-Methylpropionamide was employed as an HPLC internal, instrument standard. Values for product yields and starting material recovery are all based on this internal instrument calibration standard.

EXAMPLE 1

5-cyanopentanamide production from adipontrile using Pseudomonas-derived Whole Cell Biocatalysts Various Pseudomonas strains were grown on 10 mM adipontrile in PR Basal medium for 24 h and harvested by centrifugation. Wet cell pastes were frozen for storage. To test for biocatalyst reaction, 50 mg of frozen cell paste was resuspended in 1 mL of 50 mM pyrophosphate buffer, pH 7.5. Adiponitrile substrate was added to a final concentration of 100 mM and the cell suspensions were shaken at 200 rpm at 5° C. for 4–7 h. Cells were removed by centrifugation and the clarified supernatant was analyzed for the presence of 5-cyanopentanamide by gas chromatography. The following Pseudomonas strains were found to produce the desired product: *P. putida* 5B-MGN-2p (NRRL-18668), Pseudomonas sp. 3L-H-2-6-1p, *P. putida* 20-5-SBN-1b (ATCC 55735), *P. putida* 3L-G-1-5-1a-1 (ATCC 55736), *P. chlororaphis* B23 (FERM-B187), Pseudomonas sp. 3L-H-9-6-2p, and *P. putida* 2-H-9-5-1a.

EXAMPLE 2

5-cyanopentanamide Production Using Whole Cell Biocatalyst

Into a 15 mL polypropylene centrifuge tube was placed 9.08 mL of 20 mM $KH_2PO_4$/20 mM sodium butyrate buffer (pH 7.1) at 5° C., then 64 mg of 3L-G-1-5-1a-1 (ATCC 55736) wet cells and 0.853 mL (0.811 g, 7.50 mmol) of adiponitrile was added to the tube and the contents mixed on a rotating platform at 5° C. The resulting reaction volume contained 15 NHase IU/m. Aliquots (0.10 mL) were withdrawn at regular intervals, mixed with 0.010 mL of 1.0M HCl (to stop the reaction) and 0.100 mL of 0.200M N-methylpropionamide internal standard solution, and analyzed by HPLC to monitor the progress of the reaction. After 4 h, the HPLC yields of 5-cyanopentanamide and adipamide were 99.7% and 2.1%, respectively, with no adiponitrile remaining.

EXAMPLE 3

5-cyanopentanamide Production Using Immobilized Biocatalyst

The reaction described in Example 2 was repeated using 8.95 mL of 20 mM $KH_2PO_4$/20 mM sodium butyrate buffer (pH 7.1) at 5° C., 193 mg of 1 mm diameter, 10 weight % polyacrylamide gel beads containing 64 mg of 3L-G-1-5-1a-1 (ATCC 55736) wet cells, and 0.853 mL (0.811 g, 7.50 mmol) of adiponitrile. The resulting reaction volume contained 1.4 NHase IU/mL. Aliquots (0.10 mL) were withdrawn at regular intervals, mixed with 0.010 mL of 1.0M HCl (to stop the reaction) and 0.100 mL of 0.200M N-methylpropionamide internal standard solution, and analyzed by HPLC to monitor the progress of the reaction. After 6 h, the HPLC yields of 5-cyanopentanamide and adipamide were 94.4% and 1.6%, respectively, with 2.4% adiponitrile remaining.

EXAMPLE 4

Stability of Immobilized Biocatalyst for 5-cyanopentanamide Production

The reaction described in Example 3 was repeated using 8.55 mL of 20 mM $KH_2PO_4$/20 mM sodium butyrate buffer (pH 7.1) at 5° C., 600 mg of 1 mm diameter, 10 weight % polyacrylamide gel beads containing 200 mg of 3L-G-1-5-1a-1 (ATCC 55736) wet cells, and 0.853 mL (0.811 g, 7.50 mmol) of adiponitrile. The resulting reaction volume contained 4.7 NHase IU/mL. Aliquots (0.10 mL) were withdrawn at regular intervals, mixed with 0.010 mL of 1.0M HCl (to stop the reaction) and 0.100 mL of 0.200M N-methylpropionamide internal standard solution, and analyzed by HPLC to monitor the progress of the reaction. After 2 h, the HPLC yields of 5-cyanopentanamide and adipamide were 96.2% and 1.4%, respectively, with 0.8% adiponitrile remaining. The immobilized cell catalyst was recovered and reused in a total of 17 consecutive batch reactions (HPLC yields in Table 1, below); the remaining NHase activity at the end of reaction 17 was 0.94 IU/mL, corresponding to 28% of initial NHase activity. The productivity of the reaction, calculated as grams of 5-cyanopentanamide produced per gram dry cell weight of 3L-G-1-5-1a-1 (ATCC 55736), was ca. 322 g 5-cyanopentanamide/g dry cell weight (dry cell weight=0.25×wet cell weight; determined by lyophilization).

TABLE 1

| rxn # | time (h) | % 5-cyanopentanamide | % adipamide | % adiponitrile |
|---|---|---|---|---|
| 1 | 2 | 96.2 | 1.4 | 0.8 |
| 2 | 2.5 | 99.4 | 1.3 | 3.0 |
| 3 | 4 | 100.0 | 3.2 | 0.5 |
| 4 | 4 | 100.0 | 1.8 | 1.4 |
| 5 | 4 | 96.7 | 2.5 | 0.4 |
| 6 | 4 | 99.6 | 1.3 | 2.5 |
| 7 | 4 | 93.7 | 2.2 | 0 |
| 8 | 16 | 100.0 | 2.6 | 0 |
| 9 | 4 | 99.4 | 1.4 | 1.9 |
| 10 | 4 | 89.9 | 2.1 | 3.9 |
| 11 | 4 | 92.4 | 1.5 | 7.4 |
| 12 | 5 | 89.7 | 1.9 | 2.4 |
| 13 | 16 | 98.4 | 2.0 | 0 |
| 14 | 5 | 89.3 | 1.1 | 11.8 |
| 15 | 16 | 100.0 | 1.5 | 0 |
| 16 | 6.5 | 88.0 | 0.9 | 12.4 |
| 17 | 16 | 99.8 | 1.1 | 0.9 |

EXAMPLE 5

Production of ω-cyanocarboxamides from 2-methylglutaronitrile Using Whole Cell Biocatalyst To a 15 mL polypropylene test tube was added 1.14 mL (1.08 g, 10.00 mmol) of 2-methylglutaronitrile and 300 IU of 3L-G-1-5-1a-1 (ATCC 55736) cells. The total volume was adjusted to 10 mL with 20 mM $KH_2PO_4$ buffer at pH 7.0 and 15° C. The contents was mixed on a rotating platform at 5° C. Aliquots (0.10 mL) were withdrawn at regular intervals, mixed with 0.010 mL of 1.0M HCl (to stop the reaction) and 0.100 mL of 0.075M N-methylpropionamide internal standard solution, and analyzed by HPLC to monitor the progress of the reaction. After 2 h, the HPLC yields of 4-cyano-2-methylbutyramide (4-CMBAM), 4-cyanopentanamide (4-CPAM), and 2-methylglutaramide (2-MGAM) were 60.3%, 32.5%, and 5.8%, respectively, with 0.2% 2-methylglutaronitrile (2-MGN) remaining.

EXAMPLE 6

Production of ω-cyanocarboxamides from 2-methylglutaronitrile Using Whole Cell Biocatalyst The procedure described in Example 5 was repeated using 0.570 mL (0.542 g, 5.00 mmol) of 2-methylglutaronitrile, and 150 IU of 3L-G-1-5-1a-1 (ATCC 55736) cells. The total volume of the reaction mixture was adjusted to 10 mL with 20 mM KH2PO$_4$ buffer at pH 8.5 and 5° C. After 4 h, the HPLC yields of 4-cyano-2-methylbutyramide (4-CMBAM), 4-cyanopentanamide (4-CPAM), and 2-methylglutaramide (2-MGAM) were 64.3%, 26.2%, and 4.3%, respectively, with no 2-methylglutaronitrile (2-MGN) remaining.

EXAMPLE 7

Production of ω-cyanocarboxamides from 2-methylglutaronitrile Using Whole Cell Biocatalyst 1 mmole 2-MGN, 15 IU biocatalyst, pH 7, 5° C.

To a 15 mL polypropylene centrifuge tube was added 0.114 mL (0.108 g, 1.00 mmol) of 2-methylglutaronitrile (2-MGN), and 15 IU of 3L-G-1-5-1a-1 (ATCC 55736) cells. The total volume was adjusted to 10 mL with 20 mM $KH_2PO_4$ buffer (pH 7.0) at 5° C. The contents were mixed on a rotating platform at 5° C. Aliquots (0.10 mL) were withdrawn at regular intervals, mixed with 0.010 mL of 1.0M HCl to stop the reaction and 0.100 mL of 0.075M N-methylpropionamide internal standard solution, and analyzed by HPLC to monitor the progress of the reaction. After 5 h, the HPLC yields of 4-cyano-2-methylbutyramide (4-CMBAM), 4-cyanopentanamide (4-CPAM), and 2 methylglutaramide (2-MGAM) were 68.8%, 27.0%, and 4.3%, respectively, with 0.5% 2-methylglutaronitrile (2-MGN) remaining.

EXAMPLE 8

Production of ω-cyanocarboxamides from 2-Methylglutaronitrile Using Whole Cell Biocatalyst Various 2-MGN/biocatalyst loadings, pH 7, 5° C.

The procedure described in Example 7 was repeated, and both the amount of NHase activity and the amount of 2-methylglutaronitrile (2-MGN) added to a total 10 mL reaction volume were varied. Loadings of 5 mmol or greater 2-MGN are initially two phase reactions(as described in the detailed description of the invention). The yields of products and recovered 2-MGN for these reactions, as well as the reaction time for each reaction are reported in Table 2 below.

TABLE 2

| mmol 2-MGN/ 10 mL rxn | NHase IU/ 10 mL rxn | time (h) | 4-CMBAM (%) | 4-CPAM (%) | 2-MGAM (%) | 2-MGN (%) |
|---|---|---|---|---|---|---|
| 1.00 | 15 | 5.0 | 68.8 | 27.0 | 4.3 | 0.5 |
| 1.00 | 75 | 1.0 | 67.6 | 27.1 | 5.3 | 0 |
| 5.00 | 75 | 7.0 | 62.3 | 25.4 | 4.3 | 10.5 |
| 5.00 | 150 | 2.5 | 65.8 | 27.6 | 4.9 | 0.4 |
| 5.00 | 750 | 0.5 | 67.0 | 28.2 | 5.1 | 0.3 |
| 7.50 | 300 | 3.0 | 65.2 | 28.3 | 5.2 | 0.4 |
| 10.0 | 300 | 5.5 | 65.2 | 27.3 | 7.5 | 0.1 |
| 30.0 | 1000 | 25 | 63.7 | 28.6 | 6.1 | 2.2 |
| 50.0 | 1000 | 21 | 48.0 | 22.0 | 4.9 | 15.0 |

EXAMPLE 9

Production of 5ocyanopentanamide from ADN Using Whole Cell Biocatalyst 200 mM ADN, 50 mg wet cells, 20-5-SBN-1b (ATCC 55735), pH 7.5, 30° C.

In a 20 mL glass vial, 50 mg wet cell paste of 20-5-SBN-1b (ATCC 55735) was resuspended in 1 mL of 50 mM pyrophosphate buffer, pH 7.5. Adiponitrile was added to a final concentration of 200 mM and the reaction mixture was shaken at 200 rpm at 30° C. for 4 h on a rotary shaker. Cells were removed by centrifugation and the recovered aqueous solution was diluted 1:10 with 10 mM 1,1-diethyl urea internal standard in acetonitrile and analyzed by gas chromatography. Of the ADN substrate, 5% of the original material remained and 93% had been converted to the only observed product, 5-cyanopentanamide.

EXAMPLE 10

Production of 5-cyanopentanamide from ADN Using Whole Cell Biocatalyst 400 mM ADN, 50 mg wet cells, 20-5-SBN-1b (ATCC 55735), pH 7.5, 30° C.

In a 20 mL glass vial, 50 mg wet cell paste of 20-5-SBN-1b (ATCC 55735) was resuspended in 1 mL of 50 mM pyrophosphate buffer, pH 7.5. Adiponitrile was added to a final concentration of 400 mM and the reaction mixture was shaken at 200 rpm at 30° C. for 4 h on a rotary shaker. Cells were removed by centrifugation and the recovered aqueous solution was diluted (1:20 with 10 mM 1,1-diethyl urea internal standard in acetonitrile) and analyzed by gas chromatography. Of the ADN substrate, 41% of the original material remained and 50% had been converted to the only observed product, 5-cyanopentanamide.

EXAMPLE 11

Production of 4-CMBAM and 4-CPAM from Whole Cell Biocatalyst 200 mM 2-MGN, 50 mg wet cells, 20-5-SBN-1b, pH 7.5, 30° C.

In a 20 mL glass vial, 50 mg wet cell paste of20-5-SBN-1b (ATCC 55735) is resuspended in 1 mL of 50 mM pyrophosphate buffer, pH 7.5. 2-Methylglutaronitrile (2-MGN) is added to a final concentration of 200 mM and the reaction mixture is shaken at 200 rpm at 30° C. for 4 h on a rotary shaker. Cells are removed by centrifugation and the recovered aqueous solution is diluted 1:10 with 10 mM 1,1-diethyl urea internal standard in acetonitrile and analyzed by gas chromatography. Of the 2-MGN substrate, 5% of the original material remains and 93% is converted to a mixture of the only observed products: 4-CMBAM and 4-CPAM.

EXAMPLE 12

Production of 4-CMBAM and 4-CPAM from Pseudomonas-based Biocatalysts 100 mM 2-MGN, 50 mg wet cells, pH 7.5, 5° C.

Various Pseudomonas strains are grown on 10 mM in PR Basal medium for 24 h and harvested by centrifugation. Wet cell pastes are frozen for storage. To test for biocatalyst reaction, 50 mg of frozen cell paste is resuspended in 1 mL of 50 mM pyrophosphate buffer, pH 7.5. 2-Methylglutaronitrile (2-MGN) substrate is added to a final concentration of 100 mM and the cell suspensions are shaken at 200 rpm at 5° C. for 4–7 h. Cells are removed by centrifugation and the clarified supernatant is analyzed for the presence of 4-CMBAM and 4-CPAM by gas chromatography. The following Pseudomonas strains are found to produce the desired products: P. putida 5B-MGN-2p (NRRL-18668), P. putida 3L-H-2-6-1p, P. chlororaphis B23 (FERM-B 187), and P. putida 2-H-9-5-1a.

What is claimed:

1. A method to produce aliphatic ω-cyanocarboxamides of Formula I

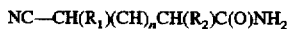

$NC-CH(R_1)(CH)_nCH(R_2)C(O)NH_2$ wherein n=1–8 and $R_1$ or $R_2$ are either H or $CH_3$, the method comprising (a) contacting, in a medium, an aliphatic α,ω-dinitrile of Formula II

$NC-CH(R_1)(CH)_nCH(R_2)CN$ wherein $n=1-8$ and $R_1$ or $R_2$ are either H or $CH_3$, with an effective amount of a *Pseudomonas putida*-derived biocatalyst having regioselective nitrile hydratase activity to produce the compound of Formula I; and (b) recovering the compound of Formula I from the medium.

2. The method of claim 1 wherein the aliphatic $\alpha,\omega$-dinitrile of Formula II is adiponitrile.

3. The method of claim 1 wherein said aliphatic $\alpha,\omega$-dinitrile of Formula II is 2-methylglutaronitrile.

4. The method of claim 1 wherein said *Pseudomonas putida*-derived biocatalyst is selected from the group consisting of *P. putida* 3L-G-1-5-1a-1 (ATCC 55736) and *P. putida* 20-5-SBN-1b (ATCC 33735).

5. The method of claim 2 wherein said *Pseudomonas putida*-derived biocatalyst is selected from the group consisting of *P. putida* 3L-G-1-5-1a-1 (ATCC 55736) and *P. putida* 20-5-SBN-1b (ATCC 33735).

6. A method for the production of 5-cyanopentanamide from adiponitrile comprising (a) contacting adiponitrile with an effective amount of *Pseudomonas putida*-derived biocatalyst derived from *P. putida* 3L-G-1-5-1a-1 (ATCC 55736) or *P. putida* 20-5-SBN-1b (ATCC 33735), and (b) recovering 5-cyanopentanamide from the medium.

7. A method according to claim 3 wherein said *Pseudomonas putida*-derived biocatalyst is selected from the group consisting of *P. putida* 3L-G-1-5-1a-1 (ATCC 55736) and *P. putida* 20-5-SBN-1b (ATCC 55735).

8. A method for the production of 4-cyanopentanamide and 4-cyano-2-methylbutyramide from 2-methylglutaronitrile comprising (a) contacting 2-methylglutaronitrile with an effective amount of *Pseudomonas putida*-derived biocatalyst derived from *P. putida* 3L-G-1-5-1a-1 (ATCC 55736) or *P. putida* 20-5-SBN-1b (ATCC 33735).

(b) recovering 4-cyanopentanamide and 4-cyano-2-methylbutyramide from the medium.

9. A method to produce aliphatic $\omega$-cyanocarboxamides of Formula I $$NC-CH(R_1)(CH)_nCH(R_2)C(O)NH_2$$

wherein $n=1-8$ and $R_1$ or $R_2$ are either H or $CH_3$, the method comprising (a) contacting, in a medium, an aliphatic $\alpha,\omega$-dinitrile of Formula II $$NC-CH(R_1)(CH)_nCH(R_2)CN$$

wherein $n=1-8$ and $R_1$ or $R_2$ are either H or $CH_3$, with an effective amount of a *Pseudomonas putida*-derived biocatalyst selected from the group consisting of *P. putida* 3L-G-1-5-1a-1 (ATCC 55736) and *P. putida* 20-5-SBN-1b (ATCC 33735), each member of the group characterized by regioselective nitrile hydratase activity to produce the compound of Formula I; and (b) recovering the compound of Formula I from the medium.

* * * * *

UNITED STATES PATENT AND TRADEMARK OFFICE
CERTIFICATE OF CORRECTION

PATENT NO. : 5,728,556
DATED : 3/17/98
INVENTOR(S) : H. Lilling

Page 1 of 2

It is certified that error appears in the above-identified patent and that said Letters Patent is hereby corrected as shown below:

Column 3, line 14, delete "NC-CH($R_1$)(CH)$_n$CH($R_2$)C(O)NH$_2$" and substitute therefor --NC-CH($R_1$)(CH$_2$)$_n$CH($R_2$)C(O)NH$_2$--.

Column 3, line 19, delete "NC-CH($R_1$)(CH)$_n$CH($R_2$)CN" and substitute therefor --NC-CH($R_1$)(CH$_2$)$_n$CH($R_2$)CN--.

Claim 1, column 12, line 57 delete "NC-CH($R_1$)(CH)$_n$CH($R_2$)C(O)NH$_2$" and substitute therefor --NC-CH($R_1$)(CH$_2$)$_n$CH($R_2$)C(O)NH$_2$--.

Claim 1, column 12, line 65, delete "NC-CH($R_1$)(CH)$_n$CH($R_2$)CN" and substitute therefor --NC-CH($R_1$)(CH$_2$)$_n$CH($R_2$)CN--.

Claim 9, column 14, line 12, delete "NC-CH($R_1$)(CH)$_n$CH($R_2$)C(O)NH$_2$" and substitute therefor --NC-CH($R_1$)(CH$_2$)$_n$CH($R_2$)C(O)NH$_2$--.

UNITED STATES PATENT AND TRADEMARK OFFICE
CERTIFICATE OF CORRECTION

PATENT NO. : 5,728,556
DATED : 3/17/98
INVENTOR(S) : H. Lilling

It is certified that error appears in the above-identified patent and that said Letters Patent is hereby corrected as shown below:

Claim 9, column 14, line 20, delete "NC-CH($R_1$)(CH)$_n$CH($R_2$)CN" and substitute therefor --NC-CH($R_1$)(CH$_2$)$_n$CH($R_2$)CN--.

Signed and Sealed this

Twenty-seventh Day of April, 1999

Attest:

Q. TODD DICKINSON

*Attesting Officer*  *Acting Commissioner of Patents and Trademarks*